United States Patent
Benk (10) Patent No.: US 11,234,725 B2
(45) Date of Patent: Feb. 1, 2022

(54) SHAFT FOR A MEDICAL INSTRUMENT, AND MEDICAL INSTRUMENT, IN PARTICULAR HOMOPOLAR OR BIPOLAR MEDICAL INSTRUMENT

(71) Applicant: Tontarra Medizintechnik GmbH, Wurmlingen (DE)

(72) Inventor: Michael Benk, Wurmlingen (DE)

(73) Assignee: Tontarra Medizintechnik GmbH, Wurmlingen (DE)

( * ) Notice: Subject to any disclaimer, the term of this patent is extended or adjusted under 35 U.S.C. 154(b) by 492 days.

(21) Appl. No.: 16/091,216

(22) PCT Filed: Apr. 6, 2017

(86) PCT No.: PCT/EP2017/058217
§ 371 (c)(1),
(2) Date: Oct. 4, 2018

(87) PCT Pub. No.: WO2017/174707
PCT Pub. Date: Oct. 12, 2017

(65) Prior Publication Data
US 2019/0110806 A1    Apr. 18, 2019

(30) Foreign Application Priority Data

Apr. 7, 2016   (DE) ............... 10 2016 106 397.5

(51) Int. Cl.
*A61B 18/12*   (2006.01)
*A61B 17/29*   (2006.01)
(Continued)

(52) U.S. Cl.
CPC .......... *A61B 17/29* (2013.01); *A61B 18/1445* (2013.01); *A61B 18/1447* (2013.01);
(Continued)

(58) Field of Classification Search
CPC ............ A61B 18/1445; A61B 18/1447; A61B 2018/00595; A61B 2018/00601;
(Continued)

(56) References Cited

U.S. PATENT DOCUMENTS 5,295,990 A * 3/1994 Levin ................ A61B 10/06
                                                   600/564
5,478,350 A * 12/1995 Kratsch ............ A61B 17/29
                                                   600/564
(Continued)

FOREIGN PATENT DOCUMENTS

DE     101 56 917 A1    6/2003
DE     102 36 070 A1    3/2004
(Continued)

OTHER PUBLICATIONS

International Search Report for corresponding Patent Application No. PCT/EP2017/058217 dated Sep. 26, 2017.

*Primary Examiner* — Daniel W Fowler
(74) *Attorney, Agent, or Firm* — Renner, Otto, Boisselle & Sklar, LLP (57) ABSTRACT

The invention relates to a shaft for a medical instrument (12), in particular a homopolar or bipolar medical instrument, comprising a shaft member (16) that accommodates a tool (18) at the distal end, said tool (18) being provided with a first jaw part (19) and a second jaw part (21) which can be moved relative to each other from an open position (29) into a closed position (28) by a draw bar/push rod (26) that is guided inside the shaft member (16); at the proximal end, the shaft member (16) has a connecting piece (14) for attachment to a manipulating device (23) that allows the draw bar/push rod (26) to be moved back and forth; at the distal end, each jaw part (19, 21) is pivotally guided inside the shaft member (16) by means of a sliding block (49).

18 Claims, 9 Drawing Sheets

(51) Int. Cl.
*A61B 18/14* (2006.01)
*A61B 18/00* (2006.01)

(52) U.S. Cl.
CPC .............. *A61B 2017/2901* (2013.01); *A61B 2018/0063* (2013.01); *A61B 2018/00595* (2013.01); *A61B 2018/00601* (2013.01); *A61B 2018/1405* (2013.01); *A61B 2018/146* (2013.01); *A61B 2018/1425* (2013.01)

(58) Field of Classification Search
CPC .... A61B 2018/0063; A61B 2018/1405; A61B 2018/1425; A61B 2018/146
See application file for complete search history.

(56) References Cited

U.S. PATENT DOCUMENTS

| | | | | |
|---|---|---|---|---|
| 5,618,304 | A * | 4/1997 | Hart | A61B 17/0467 606/205 |
| 5,849,022 | A * | 12/1998 | Sakashita | A61B 17/29 606/174 |
| 6,599,309 | B1 * | 7/2003 | Gilman | A61B 17/1608 606/205 |
| 7,559,940 | B2 * | 7/2009 | McGuire | A61B 17/1608 606/184 |
| 2002/0019596 | A1 * | 2/2002 | Eggers | A61B 18/1482 600/564 |
| 2003/0199870 | A1 * | 10/2003 | Truckai | A61B 18/1442 606/51 |
| 2004/0098041 | A1 * | 5/2004 | Wagner | A61B 17/29 606/205 |
| 2006/0271042 | A1 * | 11/2006 | Latterell | A61B 18/1445 606/51 |
| 2011/0251613 | A1 | 10/2011 | Guerra et al. | |
| 2013/0345701 | A1 | 12/2013 | Allen, IV et al. | |
| 2015/0105820 | A1 | 4/2015 | Fan et al. | |

FOREIGN PATENT DOCUMENTS

| | | |
|---|---|---|
| DE | 20 2004 010 780 U1 | 9/2004 |
| DE | 10 2006 056405 A1 | 7/2008 |
| DE | 20 2011 052 418 U1 | 2/2012 |
| EP | 2 653 117 A1 | 10/2013 |

* cited by examiner

SHAFT FOR A MEDICAL INSTRUMENT, AND MEDICAL INSTRUMENT, IN PARTICULAR HOMOPOLAR OR BIPOLAR MEDICAL INSTRUMENT

The invention relates to a shaft for a medical instrument as well as a medical instrument, in particular a mono- or bipolar medical instrument.

A medical instrument for endoscopic surgery is known from DE 101 56 917 A1. A tubular shaft is fastened at its proximal end to a housing which has grip parts, in order to actuate a pull/push rod which is guided in the tubular shaft. By means of these, a tool arranged at the distal end of the shaft, said tool having two mouth parts, is transferred from an opening position into a closing position or grip position. The two mouth parts forming the tool are pivotably supported in the shaft by a common pivot axis which is fixedly arranged on the shaft. During the opening and closing of the mouth parts, pivot arms of the mouth parts or so-called hinges protrude opposite an outer periphery of the shaft body. Such an arrangement has the disadvantage that the mouth parts which are respectively supplied with electricity and the hinges protruding opposite the shaft body can lead to injuries near the working region of the mouth parts.

An analogous surgical instrument for electrosurgery is known from DE 20 2004 010 780 U1.

This applies analogously for an electrical surgical instrument according to DE 20 2011 052 418 U1, in which only an articulated arm of the moveable mouth part emerges during the transfer into an opening movement relative to a cylindrical shaft body.

The object of the invention is to create a shaft for a medical instrument as well as a medical instrument, in particular a mono- or bipolar medical instrument, for electrosurgery, in which actuating members for introducing the opening and closing movement of the mouth parts remain within a shaft during the opening and closing movement of the at least one mouth part.

This object is solved by a shaft for a medical instrument, in which the at least one mouth part is guided at the distal end in the shaft body by at least one connecting link, wherein an arcuate segment-shaped track and a guideway running coaxially thereto is provided and an actuating member of the mouth part is formed to be curved in a complementary manner, and is guided along the track and the guideway with an outer and inner guide surface, wherein a carriage in the shaft body is displaceably guided along the longitudinal axis of the shaft body, said carriage being moveable by means of the pull/push rod and transferring the at least one mouth part into an opening position and a closing position. By means of such a connecting link, a path-controlled or curve-controlled opening and closing movement of the mouth part or parts can be achieved without components of the mouth part or parts such as, for example, actuating members that are controlled for the opening and closing movement, projecting opposite an outer periphery of the shaft. A closed shaft body can be provided from the proximal end to the distal end by means of the connecting link guided or path-controlled opening and closing movement of the at least one mouth part, such that only the working regions of the mouth parts are provided distally outside the shaft body. Any drive components for carrying out the opening and closing movement of the at least one mouth part are provided within a closed shaft body. This articulation axis-free receptacle of the mouth part or parts enables the closed formation of the shaft body outwardly in the peripheral direction. In particular with use for a mono- or bipolar medical instrument, it is thus ensured that a current flow takes place exclusively in the working region of the mouth parts, because no current-carrying components of the mouth parts or of a drive of the mouth parts emerge laterally or radially from the outer peripheral surface of the shaft.

Furthermore, it is preferably provided that a connecting link to the separate receptacle is respectively provided for each mouth part at the distal end in the shaft body. This enables each actuating member provided on the mouth part to be guided separately in a connecting link. Here, it can be provided that the connecting links border on each other directly and partially form a common connecting link space. An especially space-efficient arrangement can thus be created, in order to create, in particular, thin diameters for minimally invasive surgery. In this case, the portions of the actuating members, said portions optionally abutting one another, can be provided with an isolation or an isolating coating. It is preferably provided that each connecting link is arranged within an outer periphery of the shaft body. The actuating member of the mouth part is thus prevented from emerging opposite an outer periphery of the shaft body and the diameter of the shaft body can be maintained over the entire length.

It is preferably provided that two connecting links which are adjacent to each another and separate from each another are provided at the distal end of the shaft body, in which an actuating body of the mouth part is respectively provided. This has the advantage that the actuating members which are positioned within the shaft body in the respective connecting link and displaceably guided are arranged separately from one another. In a mono- or bipolar medical instrument, a simplified current conduction can be enabled for each mouth part.

The at least one connecting link preferably has an outlet opening which is in an end face of the shaft body. The adjacent outer peripheral surface of the shaft body can thus be closed. Additionally, the end face of the shaft body is closed with the exception of the at least one opening leading to at least one connecting link. The actuating member of the mouth part is guided through this opening in the connecting link.

A further preferred embodiment of the shaft provides that the connecting link has an arcuate segment-shaped track and a guideway running coaxially thereto and the actuating member is formed to be curved in a complementary manner and is guided with an inner and outer guide surface along the track and guideway. An opening and closing of the mouth parts can be achieved during a sliding movement acting on the actuating member in and against the longitudinal axis of the shaft by means of this track, which is formed to be arcuate segment-shaped. During opening of the mouth parts, only one sub-region of the actuating member is moved from the mouth part out of the distal end of the shaft body or guided out, though an end face of the shaft body can generally be formed to be closed at the distal end.

Furthermore, it is preferably provided that the two connecting links which are opposite each other are oriented point-symmetrically to the longitudinal axis of the shaft body. It is thus enabled that a synchronous course is enabled during opening and closing of the two mouth parts with the two connecting links arranged with respect to one other.

It can alternatively be provided that the connecting links arranged opposite one another have courses which deviate from one another. An asynchronous movement of the mouth parts can thus be achieved. For example, a mouth part can have a greater range of motion than the opposite mouth part.

Furthermore, a mouth part can be transferred into a slanted position at a different point in time from the at least one further mouth part.

Furthermore, it is preferably provided that the actuating members of the two mouth parts are curved in opposite directions. Depending on the design of the working region of the mouth parts, there can thus be identical parts, provided that, for example, a cutting or a clamping working region is provided, identical parts can be provided for the mouth parts. Provided that, in a gripping working region, a toothing or ribbing is provided, the basic structure of the mouth parts is identical in turn, with the exception of the toothing and ribbing.

The connecting link is advantageously formed to be closed within the shaft body. This connecting link can have a rectangular, square, round, oval or semi-circular cross-section. The mouth part is thus guided non-rotatably. An opening and closing movement can thus be controlled in a targeted manner. At the same time, a rotation or tilting of the mouth parts relative to each another is prevented during closing of the mouth parts and gripping of a tissue.

Furthermore, it is preferably provided that the actuating member of the mouth part is formed to be rod-like and curved. It preferably has a complementary course and geometry relative to the connecting link. Guiding can thus take place in a simple manner in the connecting link. There can thus be very simple guiding.

The actuating member of the mouth part is preferably provided eccentrically relative to the longitudinal axis of the working region of the mouth part. This is then the case when the working regions are as wide as in a gripping or clamping function, for example. It can furthermore be provided that the actuating member of the mouth part is provided laterally offset relative to the working region of the mouth part. This is then the case in particular with a cutting function, this such that a simple attaching of the two scissor parts to the shaft is enabled.

A guide pin is preferably provided at the end of the actuating member of the mouth parts, said guide pin engaging in a guide groove on a carriage which is moveable by means of the pull/push rod in the shaft body. This guide pin enables a simple coupling of a carriage with the at least one guide pin of the at least one moveable mouth part, preferably of the two guide pins of the respective actuating member, such that there is an opening and closing of the mouth part or parts in a simple manner by a sliding movement of the carriage. This guide pin additionally enables a simple mounting.

The carriage within the shaft body preferably has two guide grooves which are opposite each other and open outwardly, and the carriage is displaceably guided between the two connecting links in the region of the guide grooves. There is thus a space-saving drive for the mouth parts. This furthermore enables both simultaneous control of the actuating members of the mouth parts and a simple constructive design.

It is furthermore preferably provided that the guide grooves of the carriage are oriented at a right angle to the working movement or displacement movement of the carriage along the longitudinal axis in the shaft body. Thrust forces and pulling forces can thus be transferred in a simple manner in order to control the opening and closing of the mouth part or the mouth parts.

The carriage in the shaft body is preferably formed as a longitudinal guide body which is non-rotatably displaceably guided in the shaft body. A square cross-section is advantageously provided, in particular having rounded corners, such that this it is not canted and thus is arranged non-rotatably.

The mouth parts can be made of metal, plastic, ceramic or similar. Provided that the mouth parts are provided for a monopolar or bipolar instrument, the non-conductive materials of the mouth parts can be provided at least regionally with a conductive coating or conductive components. Depending on the application and the design, whether it is a one-way shaft or a multi-way shaft, these materials can be selected for the mouth parts. Alternatively, a conductive coating can be applied.

For energisation of the mouth part or mouth parts with a mono- or bipolar medical instrument, it is preferably provided that at least one curved outer surface of the actuating member forms a contact point for an electrode. There can thus be contacting independently of the opening and closing movement. It can alternatively be provided that, for example, only one end region of the actuating member is provided with a conductive coating or with a conductive region, said region being conductively connected to the gripping surface of the mouth part. It is thus enabled that, for example, energisation of the mouth parts takes place only during an end phase of the closing movement or after the mouth parts have been virtually closed. The opened mouth parts can thus remain non-energised.

It is preferably provided that the at least one electrode provided in the shaft body is arranged separately to the displaceable carriage. An opening and closing movement of the mouth parts can thus take place without an actuation or movement of the at least one electrode being simultaneously necessary here. The number of parts which are moved in the shaft body is thus reduced.

It is preferably provided that one or two electrical conductors are respectively provided with a contact element, in particular a sliding contact, which is contacted with the actuating member of the mouth part. Such sliding contacts transfer the current during an opening and closing movement of the mouth part. Such sliding contacts are simultaneously wear-resistant. The sliding contact is preferably formed as an arcuate metallic spring element, such that under pre-stress, this sliding contact abuts the actuating member of the mouth part.

It is furthermore preferably provided that the mouth parts have a cutting, gripping, clamping, spoon mouth-shaped working region or are formed as forceps or a needle electrode.

The object of the invention is furthermore solved by a shaft which comprises a shaft body made of a first and a second body half which are formed to be half-shell shaped and which can be connected to a closed shaft body. This two-part design of the shaft body enables there to be a simple mounting of the components, in which, for example, a pull/push rod and a carriage coupled thereto as well as one or more moveable mouth parts which are driven by means of the carriage for opening and closing are inserted into a first body half in order to subsequently connect the second body half to the first body half and to achieve a fully closed shaft body from the proximal to the distant end, in particular with respect to an outer peripheral surface of the shaft. Provided the shaft is used for a mono- or bipolar medical instrument, one or both electrodes can be inserted or used before the two body halves are brought together.

Furthermore, it is preferably provided that the first and second body half are separated substantially along the longitudinal central plane of the shaft. This enables mounting to be begun with one or with the other body half, without a preference of one of the two body halves being necessary.

The first and second body half of the shaft body is preferably formed identically. This enables a cost reduction during production.

Advantageously, the two body halves can be fixed to each other by a latching connection or clip connection. This enables a simple connection of the two body halves and furthermore creates a step-free and closed outer peripheral surface, in particular along the longitudinal edges of the abutting body halves.

A further preferred embodiment of the shaft provides that the first and second body half is formed as an injection-moulded part, in particular produced from a plastic. A thermoplastic plastic, in particular polyoxymethylene (POM) or similar, can preferably be used. There can thus be a cost-efficient production of a one-way shaft. It can alternatively be provided that the first and second body half is also formed from a ceramic.

The first and second body half preferably each have a central cavity along the longitudinal central axis for receiving the pull/push rod. This represents the simplest embodiment, provided that only the pull/push rod is to be received within the shaft.

For a mono- or bipolar instrument, the first and second body halves of the shaft can have a depression adjacent to the central cavity for receiving an electrode and opposite, on the other side of the receptacle, can comprise an elevation. The electrode or electrodes are thus automatically fixed in the respective depression when the two body halves are brought together, because the elevation of the one body half engages in the depression of the other body half at least partially.

Furthermore, a positive latching element is preferably provided along a first longitudinal side and a negative latching element is preferably provided along a second longitudinal side. A simple plug connection, latching connection or clip connection for connecting the two body halves to a shaft can thus take place. Additionally, connections can be formed in a simple manner of plastic, in particular as an injection-moulded part. By means of this above-mentioned structure, the first and second body halves can be formed identically and nevertheless be combined into a common shaft body, wherein the positive and negative latching element form a latch connection. Adjacently to the central cavity of the pull/push rod, a closed receptacle for the electrode is formed, in each case separately, after the assembly of the shaft body, said receptacle being guided from the proximate end to the distal end and contacted with the respective mouth part at the distal end.

Furthermore, a half of the connecting piece is preferably respectively moulded at the proximal end region of the first and second body half, said halves being able to be connected to one another by further latching elements. The entire shaft can thus be formed of two body halves and nevertheless enable a receptacle on the handling device without additional components. The shaft can be connected to the handling device by a clip, latching or plug connection via this connecting piece. At the same time, the shaft can be received rotatably about its longitudinal axis relative to the handling device.

A further preferred embodiment of the shaft provides that the proximal end of the shaft has a guide portion by means of which the shaft is received, in particular rotatably, guided in the handling device.

Furthermore, at least one recess is provided on each half of the connecting piece and/or the guiding portion, a contact element, in particular a clamp-shaped, lug-shaped or pin-shaped contact element, being insertable into said recess, said contact element being conductively connected to the electrode, wherein at least one contact element is on an outer peripheral wall of the guiding portion. Thus, not only fixing but also simultaneously contacting with an electrical connecting contact can be enabled in a simple manner after the insertion of the proximal end region of the shaft into the handling device, also while maintaining rotatable receiving of the shaft relative to the handling device.

Furthermore, the pull/push rod is preferably guided out at the proximal end opposite the guiding portion and preferably has a connecting element which can be latched to a moveable handle of the handling device. There can thus be a simple joining of the pull/push rod to the moveable handle in order to subsequently actuate the mouth parts.

The invention and further advantageous embodiments and developments of the same are described and explained in the following using the examples depicted in the drawings. The features that can be seen in the description and the drawings can be applied individually or together in any combination according to the invention. Here are shown.

Figure 1:
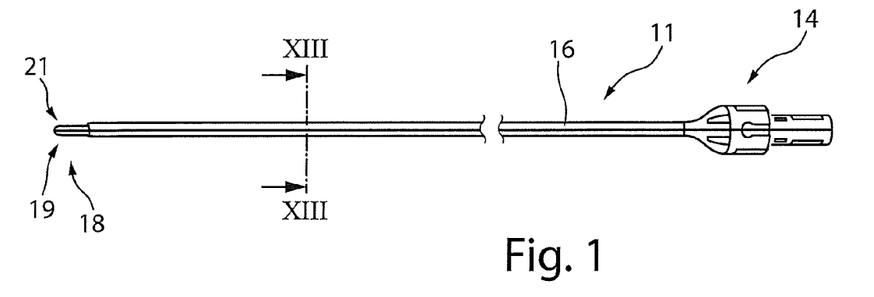
FIG. 1 a perspective view of the shaft according to the invention for a mono- or bipolar medical instrument, FIG. 2 a schematic view of a bipolar medical instrument, FIG. 3 a schematic view of a distal end of the shaft according to FIG. 1 having a tool in the closing position, FIG. 4 a perspective view of the tool according to FIG. 3 in an opening position, FIG. 5 a first perspective view of a mouth part, FIG. 6 a second perspective view of a mouth part, FIG. 7 an enlarged depiction of a distal end of a first body half of the shaft, FIG. 8 a perspective view of a larger distal region of the first body half of the shaft, FIG. 9 a perspective view of a distal end of the shaft according to FIG. 3 having a detached upper body half of the shaft, FIG. 10 a perspective view according to FIG. 9 having the tool in the opening position, FIG. 11 a schematic side view in cross-section of the distal region of the shaft according to FIG. 3, FIG. 12 a perspective view of a first body half of the shaft body in the central region of the shaft, FIG. 13 a schematic sectional view along the line XIII-XIII in FIG. 1, FIG. 14 a schematic view of a proximal end region of a first body half of the shaft, FIG. 15 a schematic partial view of a push rod having electrodes, FIG. 16 a perspective sectional view of a connecting region of the shaft and the handling device, FIG. 17 a perspective view of an alternative embodiment of a shaft having a stationary and moveable mouth part in a closing position, FIG. 18 a perspective view of the embodiment according to FIG. 17 having an opened mouth part, FIG. 19 a schematic view from above of the embodiment according to FIG. 17 and FIG. 20 a perspective view of a distal end of the shaft according to FIG. 1 having an alternative tool.
Figure 2:
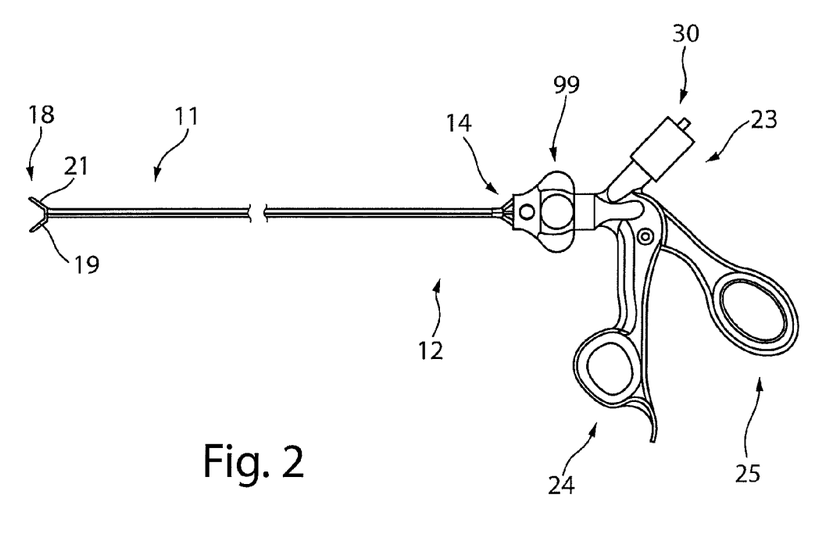

In FIG. 1, a shaft 11 for a surgical instrument 12 according to FIG. 2 is depicted. This shaft 11 comprises a connecting piece 14 at the proximal end as well as a shaft body 16 which extends between the connecting piece 14 and a tool 18 arranged at the distal end of the shaft 11. The tool 18 comprises a first and second mouth part 19, 21 which are preferably both moveable relative to each other.

Such a shaft 11 can be inserted for the surgical instrument 12 according to FIG. 2 and can be fastened to a handling device 23. This handling device 23 comprises two grip parts 24, 25 which are moveable relative to each other, whereby a pull/push rod 26 (FIG. 9) arranged in the shaft body 16 can be actuated in order to transfer the tool 18 from a closing position 28 according to FIG. 3 into an opening position 29 according to FIG. 4 and subsequently to close it again.

The handling device 23 can have a connector 30 to which a connecting cable of a current supply not depicted in further detail, for example a high-frequency surgical instrument, can be connected. Such a connector 30 can be formed as a two-polar connector socket, i.e. it has two poles which are electrically insulated from each other for a bipolar medical instrument 12. One of the poles is intended for the first mouth part 19 and the other pole is intended for the second mouth part 21.

Likewise, the connector 30 can also have only one one-pole connector socket for a monopolar medical instrument.

This surgical instrument 12 can be used in minimally invasive surgery for treating tissue in human or animal bodies with a high frequency current. The instrument 12 is to be operated both in a monopolar and bipolar manner.

Figure 3:
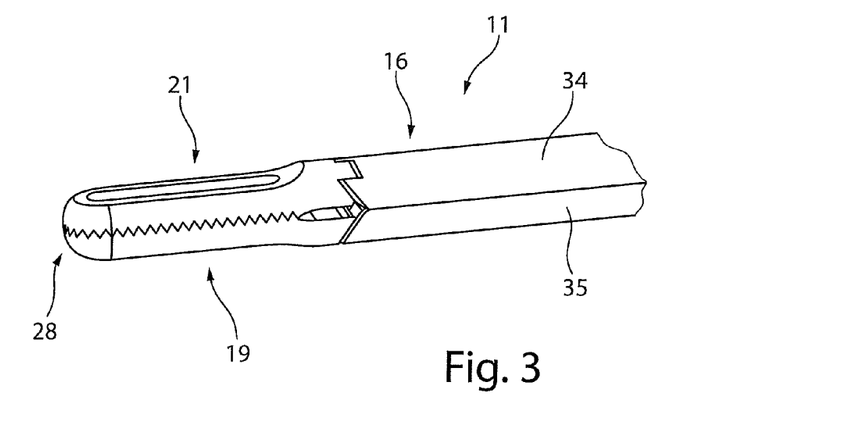

In FIG. 3, a proximal end region of the shaft body 16 having the first and second mouth part 19, 21 is depicted in a closed position 28, schematically enlarged. The shaft body 16 is formed to be closed as far as the mouth parts 19, 21. The mouth parts 19, 21 are attached on the end face to the shaft body 16. The shaft body 16 has a closed outer lateral surface from the distal up to the proximal end.

Figure 4:
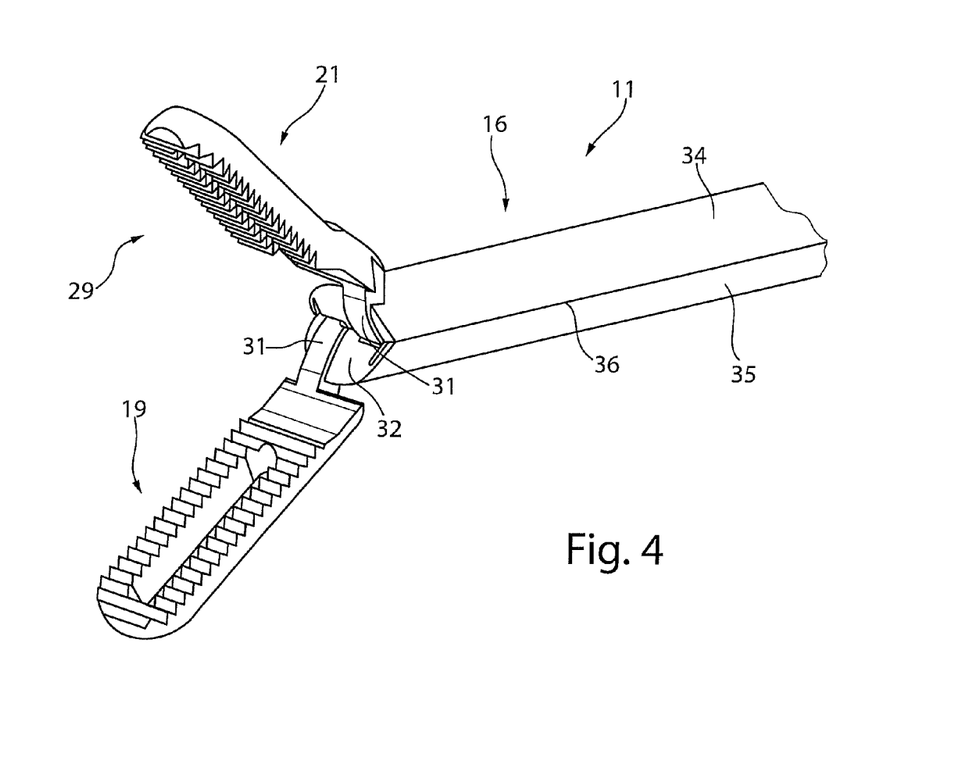

In FIG. 4, a distal region of the shaft body 16 having a first and second mouth part 19, 21 is depicted in perspective in an opening position 29. The first and second mouth part 19, 21 has an actuating member 31 in each case, which is guided slightly out opposite an end surface 32 in order to transfer the mouth parts 19, 21 into the opening position. The shaft body 16 is formed in two parts and has a first and second body half 34, 35. These preferably have a separating plane 36 in the longitudinal central axis, or the respective longitudinal edges of the first and second body half 34, 35 are in the separating plane 36.

The first mouth part 19 is depicted in a perspective view from above according to FIG. 5, in a perspective view from below according to FIG. 6. This mouth part 19 has a working region 38 which is formed, for example, as a clamping region. The actuating member 31 adjoins the end of the working region which is offset laterally relative to the longitudinal central axis of the mouth part 19. The actuating member 31 is provided in one piece on the mouth part 19, 21. This actuating member 31 is formed to be rod-like and comprises a curved course. The rod-like actuating member 31 is formed to be substantially rectangular or square, seen in cross-section, and comprises an upper and lower guide surface 41, 42 which run coaxially relative to each other. A guide pin 43 is provided on the end of the actuating member, said guide pin projecting in the direction of the longitudinal axis of the mouth part 19. A setback 45 is provided between the guide pin 43 and a web portion 44 in order to form a free space so that a carriage 47 (FIGS. 9 and 10) can engage the guide pin 43. Only the clawing in the working region 38 is adapted in such a manner that the first and second mouth part 19, 21 can be transferred into the closing position 28 depicted in FIG. 3.

Figure 7:
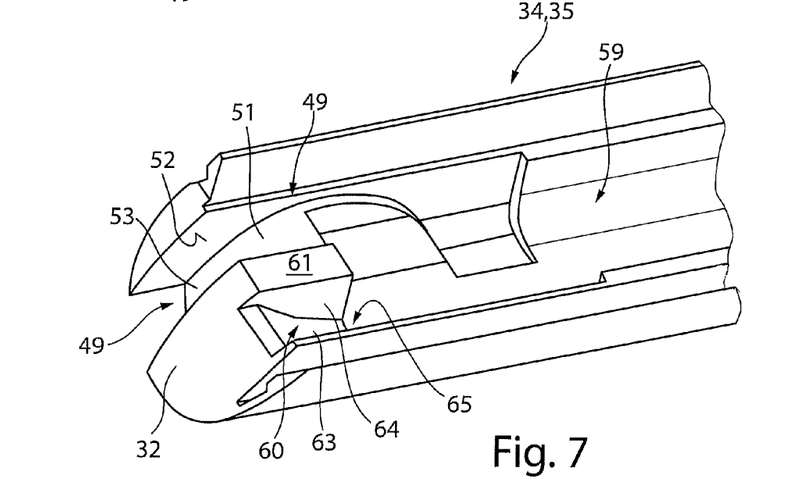

In FIG. 7, a distal region of the first or second body half 34, 35 of the shaft body 16 is depicted, schematically enlarged, wherein this is subsequently described for the first body half 34 and applies analogously for the second body half 35. A first connecting link 49 is provided contiguously with the end face 32, said connecting link comprising a curved course. The connecting links opens into the end face 32. From there, the connecting link extends as an arcuate segment in the direction of the proximal end. This connecting link 49 comprises a track 51 which is set back relative to the end face 32. The track 51 is bordered by side wall portions 52, 53. A lateral guiding of the actuating member 31 is thus enabled, such that this actuating member can be arranged in the open state according to FIG. 4. The track 51 tapers in the proximal direction, but the tapered region of the track 51 also serves for receiving and installation of the guide surface 42 of the mouth part 19.

A depression 54 (FIGS. 8 and 9) is provided on the inner end of the guideway 63 which can serve for arranging and receiving a contact element 56 of an electrical conductor 57 in order to connect a pole to the mouth part 19. A carriage guide 59 is arranged attached thereto in the proximal direction.

A second connecting link 60 is provided adjacent to the connecting link 49 and preferably separated by a web 61. This second connecting link 60 corresponds to the first connecting link 49. It is formed to be point-symmetrical relative to the longitudinal axis of the shaft body 16. A guideway 63 is introduced by the second connecting link 60 in the body half 34, 35. This guideway 63 is bordered by side walls 64, 65, analogously to the side wall portions 52, 53. The guide surface 41 of the actuating member 31 is cooled along this guideway 63 by the second mouth part 21.

This guideway 63 also emerges distally from the end face 32.

After the assembly of the first and second body halves 34, 35, the connecting link 49 is formed by the track 51, the guideway 63. This applies analogously for the second connecting link 60. The actuating member 31 is thus guided by the two opposite side wall portions 52, 53 or side walls 64, 65 and also by the track 51 and guideway 63 which are assigned to each other. Each actuating member 31 of the mouth part 19, 21 is guided out via an opening provided in the closed end face 32 of the shaft body 16 and engages in the connecting link 49, 60 via this opening. Preferably, the web 61 is arranged between the connecting link 49 and 60, such that electrical contacting between the two actuating members 31 or the mouth parts 19, 21 is prevented during contacting of the mouth parts 19, 21 by means of a pole.

Figure 8:
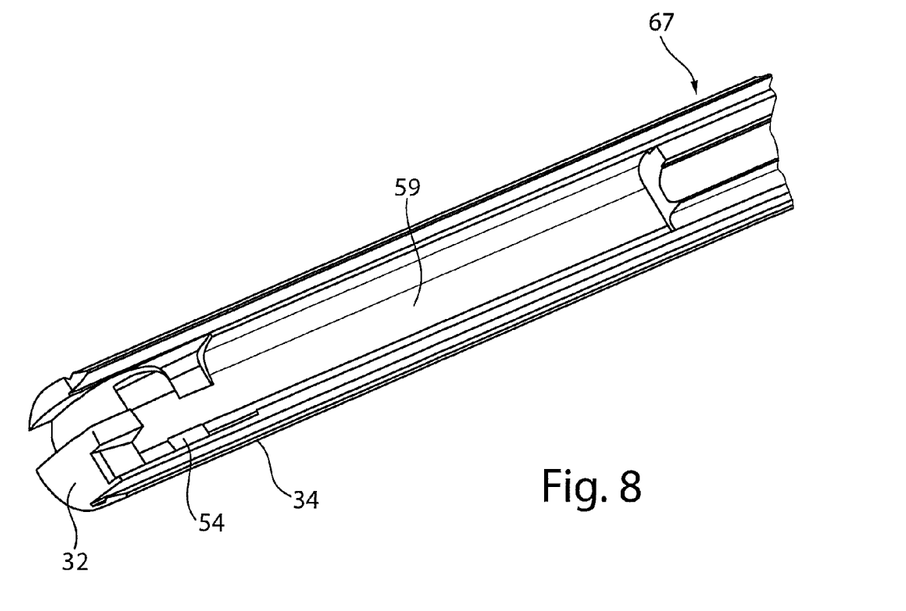

A distal region of the first body half 34, said distal region being larger relative to FIG. 7, is depicted in FIG. 8. The entire length of the carriage guide 59 is clear from this depiction. A guiding portion 67 adjoins subsequently on the proximal side, by means of which the pull/push rod 26 as well as the electrical conductor 57 are guided. This is subsequently described in more detail using FIGS. 12 and 13.

Figure 9:
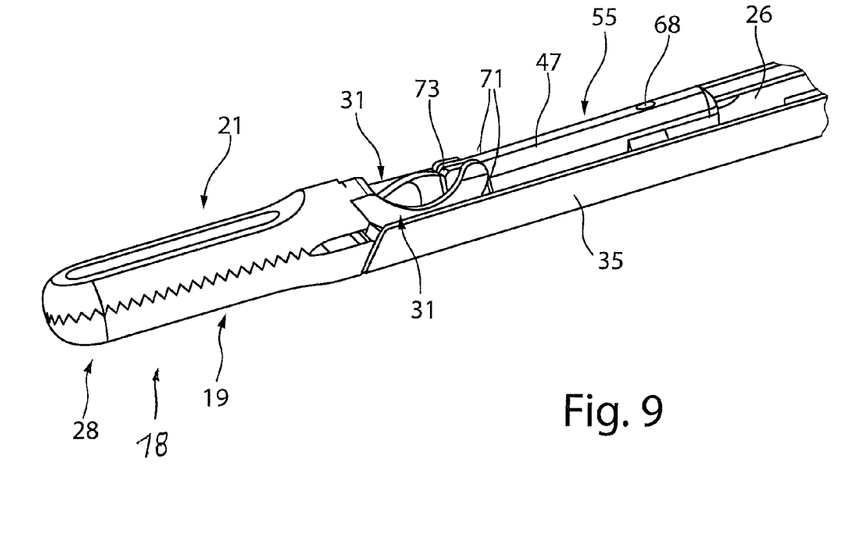

In FIG. 9, a distal end region of the shaft 11 is depicted, wherein the first body half 34 is detached from the second body half 35 in order to depict the structure and the functionality. The carriage 47 is inserted in the carriage guide 59, said carriage being drive-connected to the pull/push rod 26, for example, by a pin 68. The carriage 47 has two guide grooves 71 which are opposite each other in its front end region facing towards the end face 32, the guide pin 43 of the actuating member 31 of the first and second mouth part 19, 21 being respectively arranged and guided in said guide grooves. The first mouth part 19 is in the connecting link 49 with the guide surface 42 of the actuating member 31. The second mouth part 21 is in the second connecting link 60 with the guide surface 41 on the actuating member 31. The actuating members 31 of the first and second mouth part 32 are received by the front distal end region of the first body half, completely separated from each other.

Because the front end region of the first body half 34 is formed identically to the second body half 35, it is obvious that, in the closed shaft body, the track 51 abuts the guide surface 42 of the second mouth part and the guideway 63 abuts the guide surface 41 of the first mouth part 19. Two closed connecting links 49, 60 are thus formed which are arranged separately from each other and also each form a separate track guide for the respective actuating members 31 of the first and second mouth parts 19, 21. The region on the actuating member 31 enables an end face side end 73 of the carriage 47 to be displaced in a collision-free manner.

As soon as the grip parts 24, 25 the handling device 23 are moved towards one another, the pull/push rod 26 is displaced in the distal direction, whereby the carriage 47 is moved towards the end face 32 of the shaft body 16. Here, a pivot movement of the first and second mouth part 19, 21 along the respective connecting link 49, 60 is initiated, wherein the thrust movement is transferred into an opening movement of the mouth parts 19, 21 by the guide grooves 71 which are oriented at a right angle to the displacement movement of the carriage 47. The actuating members 31 are thus extended along the connecting link 49, 60, whereby the first and second mouth part 19, 21 opens and this is depicted in FIG. 11.

Figure 11:
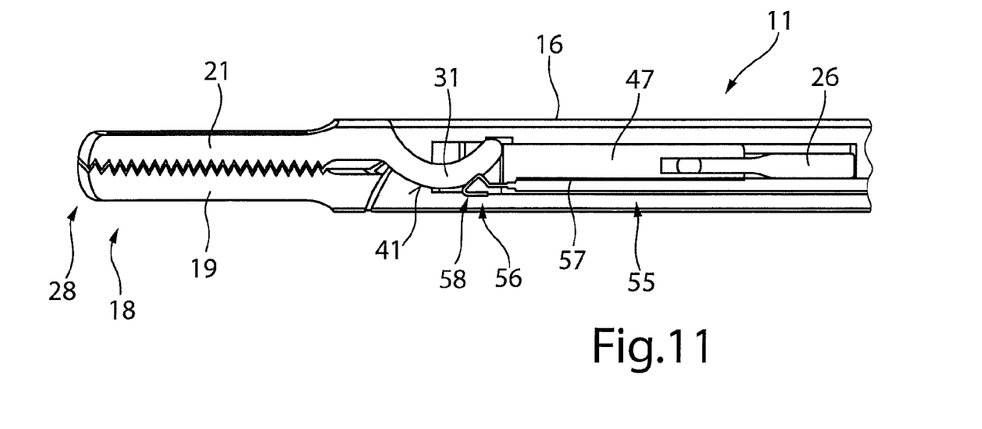

In FIG. 11, a schematic sectional view of the distal region of the shaft 11 and the tool 18 is depicted. The electrical conductor 57 is guided along the shaft 11 in the shaft body 16 for each pole, said electrical conductor contacting a guide surface 41 of the second mouth part 21 by means of the contact element 56. This contact element 56 is preferably formed as a sliding contact. Additionally, the contact element 56 is formed to be curved in a spring-like manner, such that this contact element abuts the guide surface 41 safely due to the spring tension. An analogous arrangement is provided for the second pole, in which such a contact element 56 abuts the guide surface 41 of the first mouth part 19. Each mouth part 19, 21 is thus energised by a pole. The contact remains, independently of whether the opening or closing position 28, 29 of the mouth parts 19, 21 is assumed. No additional electrically insulating measures are provided by the separate arrangement of the actuating members 31 respectively in a connecting link 49, 60. The first and second body halves 34, 35 are preferably formed of a non-conductive material. Provided that a conductive material can be used for the first and second body halves 34, 35, the connecting link 49, 60 can be lined with an electrically non-conductive material.

According to a further embodiment, the actuating member 31 can be formed conductively only in the region of the guide surface 41 with a closed arrangement of the mouth parts 19, 21, the contact element 56 abutting in said region with a closed arrangement of the mouth parts according to FIG. 11. As soon as an opening movement of the mouth parts 19, 21 out of the closing position 29 of the mouth parts 19, 21 is controlled by the carriage 47, a guide surface extending from the contact element 56 to the end of the actuating member 31 is formed non-conductively, in particular by a non-conductive coating or a non-conductive material. The current flow is thus interrupted and no current is applied to the mouth parts 19, 21 in an opening position. This enables, for example, the mouth parts 19, 21 to detect a tissue during the transfer into a closing position, but enables the mouth parts 19, 21 to be energised to coagulation only in the closing position.

In the above-mentioned embodiments, the connecting links 49 of the two actuating members 31 of the mouth parts 19 and 21 are formed point-symmetrically to a longitudinal central axis, such that a synchronous opening and closing movement of the mouth parts 19, 21 is possible.

It can alternatively be provided that the two connecting links 49 and 60 which are depicted exemplarily can be formed to deviate from one another in length, curvature and/or in course. An asynchronous closing movement of the mouth parts 19, 21 can thus be controlled. For example, a connecting link 49 can have a flatter curvature than the other connecting link. Furthermore, the length of the guideways of the connecting links 49, 60 are formed differently, such that the opening width of the mouth parts 19, 21 deviate from each other.

Figure 12:
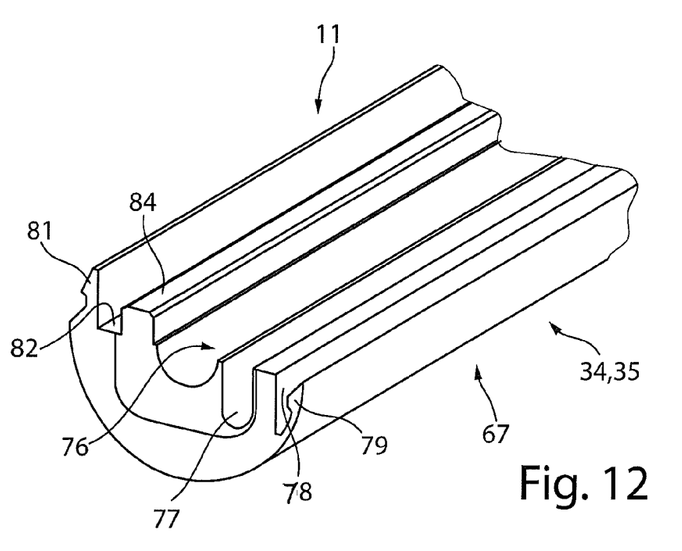
Figure 13:
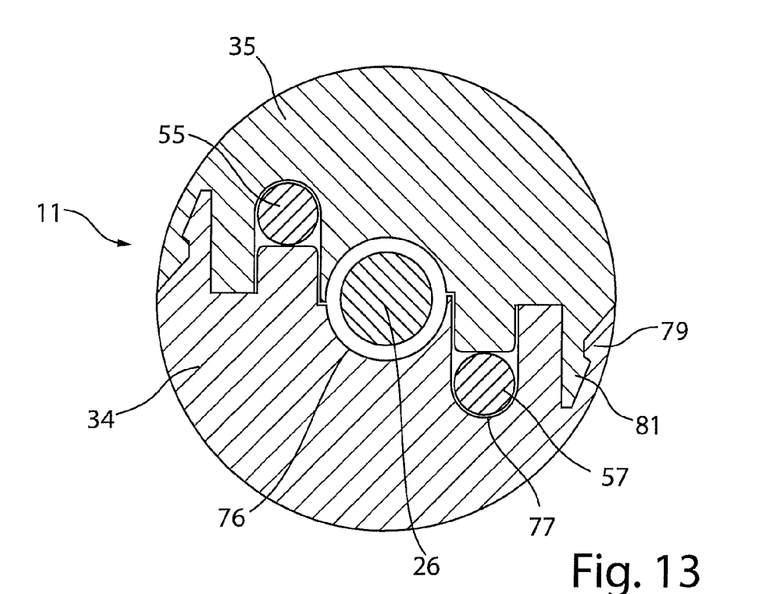

A perspective view of the guide portion 67 in the central region of the shaft 11 is depicted in FIG. 12. By this structure it is enabled that the first and second body half 34, 35 can be formed identically and nevertheless, as depicted in FIG. 13, respectively enable separate arrangement and receiving of the electrical conductor 57 and the pull/push rod 26. The first or second body half 34, 35 comprises a central receptacle 76 which is preferably formed as a semi-circle. A depression 77 is provided outwardly in a radial direction which is formed to be U-shaped in order to receive the electrical conductor. A channel 78 is formed adjacently which forms a contour for a positive latching element 79 on an inner wall. The cut-out contour is that of a negative latching element 81 which is formed physically on the opposite side. An elevation 84 is provided between the receptacle 76 and a further depression 82. As soon as the two body halves 34, 35 are guided towards one another and clipped together, a cross-sectional depiction according to FIG. 13 emerges. It is clear from this that, firstly, a circular closed receptacle 76 for the pull/push rod 26 is formed, as well as a closed receiving region for the electrical conductors 57.

Figure 5:
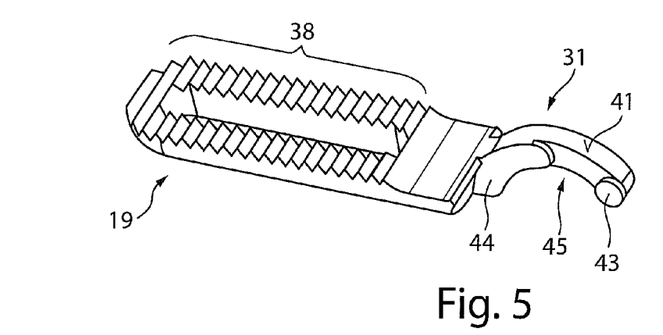
Figure 6:
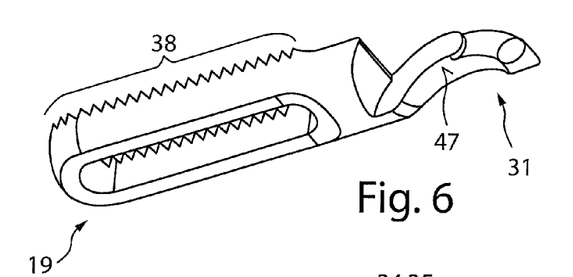

The body half 34, 35 depicted in FIG. 5 is provided for use of the shaft 11 in a mono- or bipolar medical instrument 12. Provided that neither the electrode 55 nor the electrode 57 is inserted, this shaft can also be used for a non-energised medical instrument, for example gripping forceps. In such an application, the elevation 84 and depression 77 are also not present, such that the schematic cross-section of the body half 34, 35 is simplified.

Likewise, a universally applicable shaft 11 can be formed which has the cross-section according to FIG. 12, 13 and also receives electrodes 55, 57 therein as well as the pull/push rod, wherein this shaft 11 can also be used as a handling device 23 which is formed without electrical connection. The shaft 11 can also be used for conventional surgical instruments, in particular gripping forceps.

Figure 14:
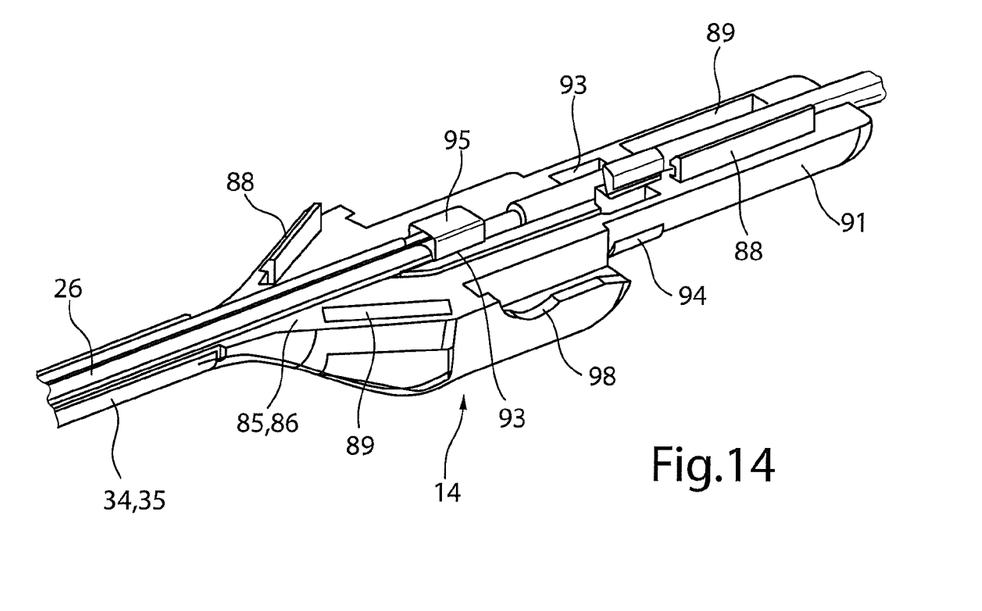

A schematic view of a proximal end region of the body half 34, 35 of the shaft 11 is depicted in FIG. 14. It is clear from this that the connecting piece 14 is also integrally connected to the shaft region of the body half 34, 35. The halves 85, 86 of the connecting piece 14, which are preferably formed integrally with the shaft region of the body halves 34, 35, likewise have latching elements 88, 89. These latching elements 88, 89 are opposite each other and are formed to be complementary, such that when the two halves 85, 86 are brought together, the two latching elements 88, 89 engage in each other and form a closed connecting piece 14.

A guide portion 91 is fitted respectively to the proximal end of the shaft 12 or of the body half 34, 35, said guide portion being provided for rotatable arrangement within the handling device 23.

Figure 16:
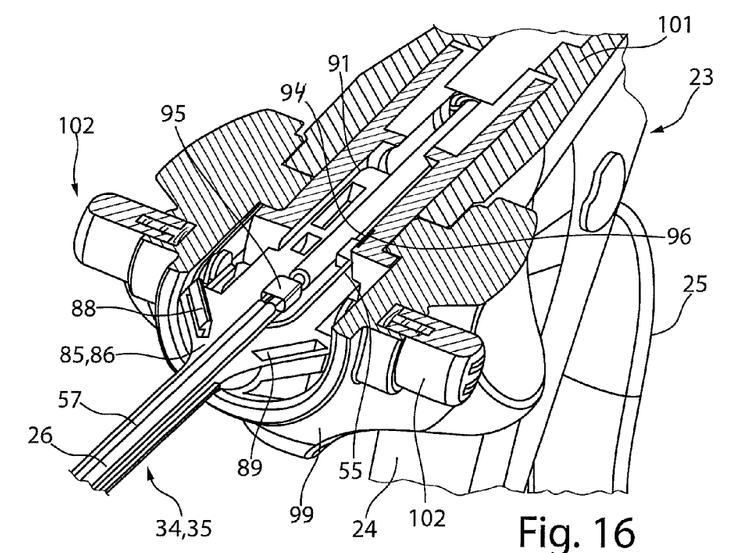

Furthermore, a recess 93 is provided both in the half 85, 86 of the connecting piece 14 and in each guide portion 91 of the body half 34, 35. Contact elements 94, 95 can be inserted into this recess 93 which are electrically conductively connected to the electrodes 55, 57. The contact element 94 which is provided in the region of the guide portion 91 is preferably on an outer peripheral surface of the guide portion 91, such that, after the insertion of the guide portion 91 into the handling device 23, an electrical contact 96 thus takes place, for example by means of a conductive ring in the housing 101 of the handling device 23 (FIG. 16). The contact element 95 can enable an electrical contacting between the pull/push rod 26 and the electrode 57.

The half 85, 85 of the connecting piece furthermore has latching surfaces 98 which form a type of eyelet after the assembly of the halves 85, 86, such that, subsequently, a releasable latching element 102, in particular a latch pin or a clip of a rotary sleeve 99, can engage on the handling device 23.

Figure 15:
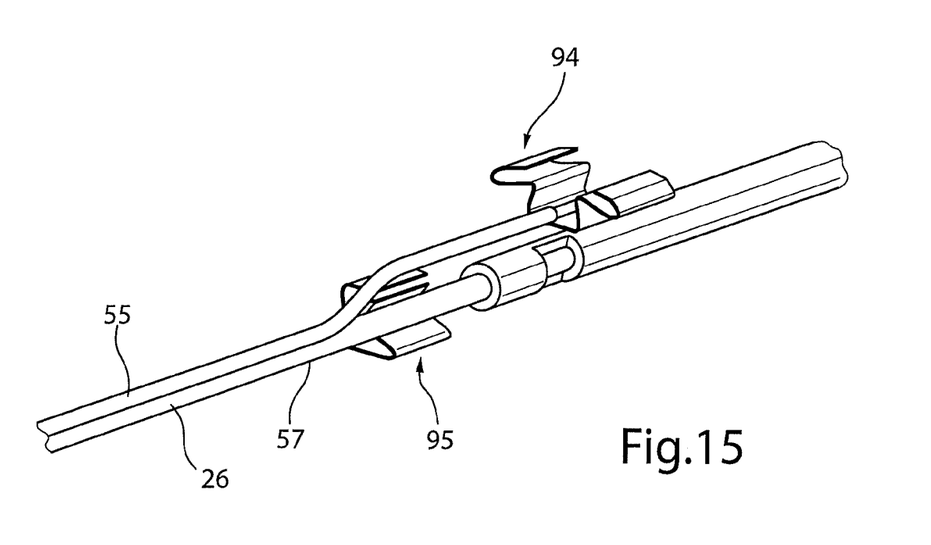

In FIG. 15, the pull/push rod 26 is depicted in perspective and enlarged, as well as the contact element 94 assigned thereto having the electrically connected electrode 55, and the positioning of the further contact element 95 which communicates with the electrode 57.

In FIG. 16, a perspective sectional view of a handling device 23 and a proximal region of the shaft 11 is depicted, which is inserted into the handling device 23. Releasable latching elements 102 are preferably provided opposite one another on the rotary sleeve 99 which is arranged rotatably relative to the housing 101 of the handling device. Here, they can be spring-loaded latching pins which engage in the latching receptacle 98 that can be formed as an open keyhole arrangement. The proximal end of the shaft 11 can thus be received releasably, but secured in place in the axial direction. The guiding portion 91 is rotatably supported in the housing 101. An electrical contact ring 96 is simultaneously provided in a peripheral surface in the housing 101, such that the contact element 34 is electrically conductively connected to the connector 30 independently of the rotary orientation. The proximal end of the pull/push rod 26 is received in a known manner with a moveable grip part 24 of the handling device 23 by means of a releasable latching, clamping or plug connection.

In this exemplary embodiment of the handling device 23, the current supply can take place for one of the two electrodes via the guide portion 91 on the shaft 11 having the housing 101. The energisation for the further electrodes can take place, for example, via the pull/push rod 26, by this pull/push rod being electrically contacted on the proximal end in the handle. The contact elements 94, 95 are arranged in the connecting piece 14 separately from one another, such that a through-contact is prevented. The positioning of the electrodes 55, 57 are also guided separately from one another, starting from the respective contact elements 94, 95 of the body halves 34, 35 in the shaft 11.

Figure 17:
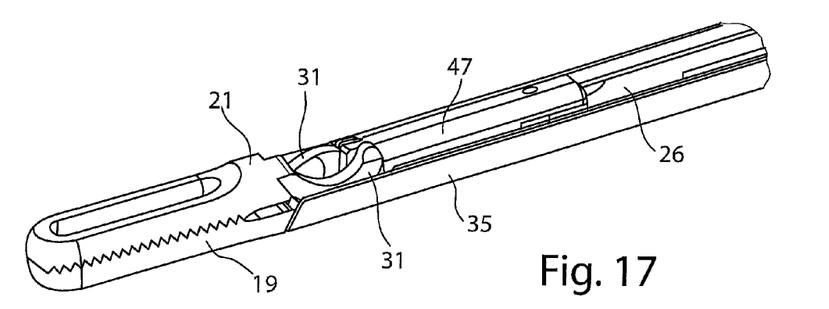
Figure 18:
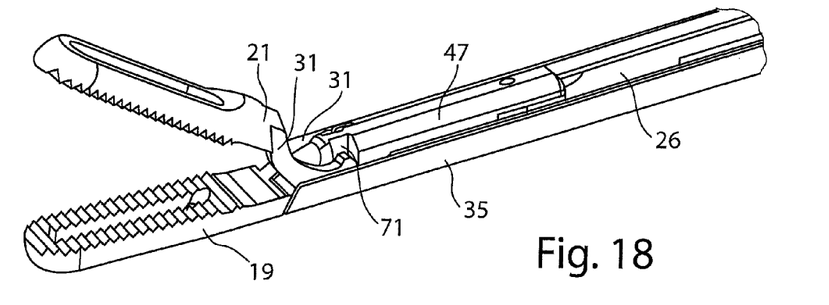
Figure 19:
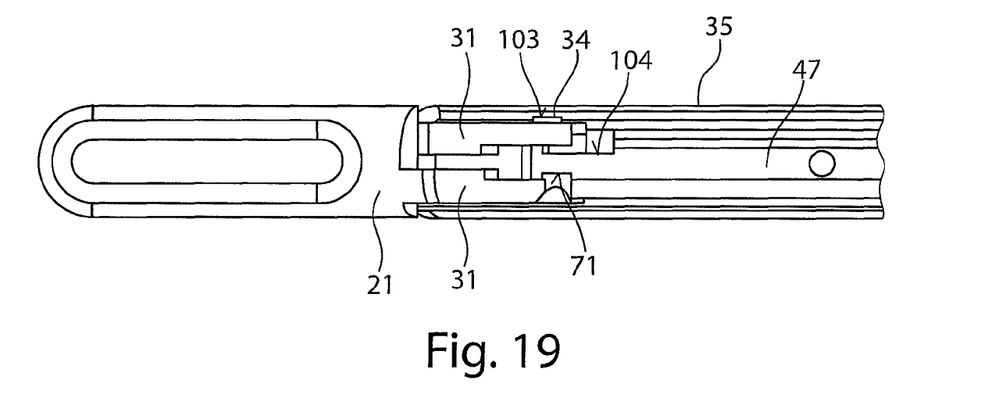

In FIG. 17, a perspective view of an alternative embodiment of the tool 18 on the shaft 11 is depicted, wherein an upper body half 34 is removed from the lower body half 35. In this embodiment it is provided that the first mouth part 19 is formed as a stationary mouth part and the second mouth part 21 is formed as a mobile mouth part, as depicted in FIG. 18. FIG. 19 shows a top view of the depiction of the shaft 11 in FIG. 17.

With regard to the embodiment of the mouth part 21 as well as the carriage 47 for the second mouth part 21 which is moved, reference is made to the above description.

Figure 10:
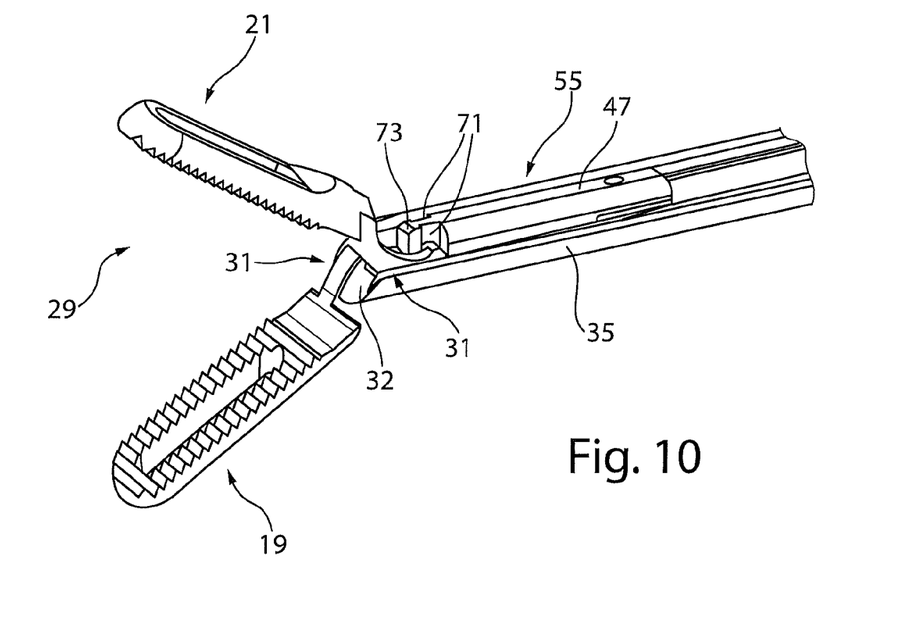

The first stationary mouth part 19 only points away from the moved mouth piece 21 such that the guide pin 43 is arranged on an opposite side of the actuating member 31, i.e., the guide pin 43 does not point towards the carriage 47 but rather in the opposite direction. The guide pin 43 is received by a U-shaped cavity 103 in the body half 35 which is formed to be open towards the separating plane between the two body halves 34, 35. Moreover, the actuating member 31 abuts the surfaces 51 or 63 of the first and second body half 34, 35 with its guide surface. By inserting the guide pin 43 into the U-shaped cavity 103 on the body half 35, a pivot movement is blocked. The carriage 47 has an enlarged cavity 104 instead of the guide groove 71, as depicted in FIG. 10, such that the carriage 47 is displaceable along the shaft 11 in order to actuate the second mouth part 21 which is moved, however is formed separately to the actuating member 31 of the stationary first mouth part 19.

Figure 20:
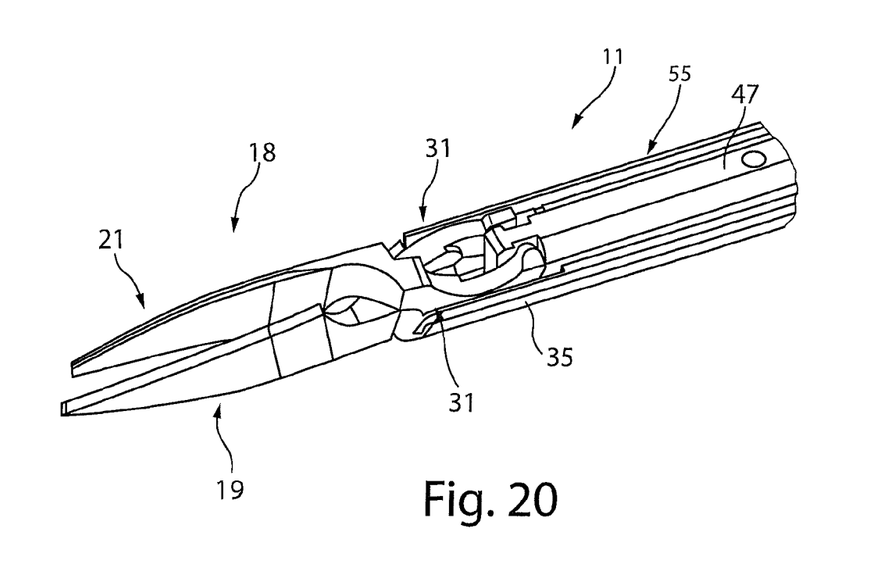

In FIG. 20, an alternative embodiment of a tool 18 for a shaft 11 is depicted. For example, the first and second mouth part 19, 21 is formed to be sharp, such that there is a cutting function. Further alternative embodiments of the mouth parts 19, 21 can likewise be provided. These can also optionally be inserted onto the shaft 11. It is only required that the actuating members 31 are adapted to the connecting links 49, 60.

The invention claimed is:

1. A medical instrument, having a shaft body extending along a longitudinal axis and a tool at a distal end of the shaft body, said tool having a first mouth part and a second mouth part, wherein the first mouth part has a first actuating part including a first curved surface and a first guide pin, and the second mouth part has a second actuating part including a second curved surface and a second guide pin, wherein first and second connections are arranged within an outer periphery of the shaft body, the first connection including a first track segment having a first arcuate surface that is complementarily shaped to the first curved surface of the first mouth part, and the second connection including a second track segment having a second arcuate surface that is complementarily shaped to the second curved surface of the second mouth part, wherein, in the shaft body, a carriage is displaceably guidable along the longitudinal axis of the shaft body, said carriage being moveable by a pull/push rod relative to the first and second connections, wherein the carriage includes first and second guide grooves, the first guide groove configured to guide the first guide pin of the first mouth part, and the second guide groove configured to guide the second guide pin of the second mouth part, wherein the first and second guide grooves of the carriage are each oriented perpendicular to a drive movement of the carriage along the longitudinal axis of the shaft body, wherein, in response to axial movement of the carriage by the pull/push rod:
pivotal movement of the first mouth part is guided by
(i) the first guide pin of the first mouth part interfacing with the first guide groove of the carriage, and
(ii) the first curved surface of the first mouth part interfacing with the first arcuate surface of the first connection; and pivotal movement of the second mouth part is guided by (i) the second guide pin of the second mouth part interfacing with the second guide groove of the carriage, and (ii) the second curved surface of the second mouth part interfacing with the second arcuate surface of the second connection.

2. The medical instrument according to claim 1, wherein said first and second connections are arranged adjacent to each other and separately from each other, and the first actuating part of the first mouth part and the second actuating part of the second mouth part are arranged in said first and second connections respectively.

3. The medical instrument according to claim 2, wherein the first and second connections are opposite to each other and are oriented point-symmetrically to the longitudinal axis of the shaft body.

4. The medical instrument according to claim 1, wherein the first actuating part of the first mouth part and the second actuating part of the second mouth part are each curved in opposite directions.

5. The medical instrument according to claim 1, wherein the first and second connections are each formed to be closed.

6. The medical instrument according to claim 1, wherein the first actuating part of the first mouth part and the second actuating part of the second mouth part are each formed to be curved in a rod-like manner, wherein the first actuating part has a cross-section which is adapted to the first connection, and wherein the second actuating part has a cross-section adapted to the second connection.

7. The medical instrument according to claim 1, wherein the first actuating part of the first mouth part and the second actuating part of the second mouth part are each provided eccentrically relative to a longitudinal central axis of the respective first and second mouth parts, or each is offset laterally relative to a working region of the first and second mouth parts.

8. The medical instrument according to claim 1, wherein the first guide pin is provided on a free end of the first actuating part of the first mouth part and the second guide pin is provided on a free end of the second actuating part of the second mouth part.

9. The medical instrument according to claim 1, wherein the first and second guide grooves are opposite each other and are open outwardly, and wherein the carriage is displaceable in a region of the first and second guide grooves between the first and second connections.

10. The medical instrument according to claim 1, wherein the carriage has an elongated guide body which is non-rotatably displaceable in a carriage guide of the shaft body.

11. The medical instrument according to claim 1, wherein the first mouth part and the second mouth part are each produced from metal, plastic or ceramic or from a non-conductive material having an at least regionally conductive coating or conductive components.

12. The medical instrument according to claim 1, wherein at least one outer surface of the first or second actuating part forms a contact point for an electrode.

13. The medical instrument according to claim 12, wherein the electrode provided in the shaft body is arranged separately to the carriage.

14. The medical instrument according to claim 12, wherein the electrode comprises an electrical conductor having a contact element and the contact element is contacted with the first or second actuating part.

15. The medical instrument according to claim 1, wherein the first mouth part and the second mouth part each have a cutting, gripping, clamping or cupped jaw-shaped working region, or are formed as forceps, or as needle electrodes.

16. The medical instrument according to claim 1, wherein the shaft body is formed of a first body half and a second body half which are formed as half shells which are connectable to form the shaft body, the first body half and the second body half of the shaft body being formed identically, wherein at a distal end of the shaft body the first and second connections are provided, the first and second connections being oriented point-symmetrically to the longitudinal axis of the shaft body, wherein the first and second connections extend into the shaft body starting from an end face of the shaft body.

17. The medical instrument according to claim 1, wherein the medical instrument is a monopolar or bipolar medical instrument.

18. The medical instrument according to claim 1, wherein each of the first mouth part and the second mouth part is articulately coupled to the carriage to permit pivotal movement of each of the first mouth part and the second mouth part without a fixed pivot axis being common to and extending through the carriage and both the first mouth part and the second mouth part, or without a common pin guiding pivotal movement of the first mouth part and the second mouth part.

* * * * *